US00PP24818P2

(12) United States Plant Patent
Wood

(10) Patent No.: US PP24,818 P2
(45) Date of Patent: Aug. 26, 2014

(54) BARBERRY PLANT NAMED 'KOREN'

(50) Latin Name: *Berberis thunbergii*
Varietal Denomination: Koren

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 181 days.

(21) Appl. No.: 13/507,792

(22) Filed: Jul. 27, 2012

(51) Int. Cl.
*A01H 5/00* (2006.01)

(52) U.S. Cl.
USPC ..... Plt./241

(58) Field of Classification Search
CPC ..... A01H 5/12
USPC ..... Plt./241
See application file for complete search history.

*Primary Examiner* — June Hwu
(74) *Attorney, Agent, or Firm* — C. A. Whealy

(57) ABSTRACT

A new and distinct cultivar of *Barberry* plant named 'Koren', characterized by its compact and mounding plant habit; vigorous growth habit; freely branching habit; leaves that are yellow to yellow green in color; good garden performance and resistance to sun scald; and resistance to Black Stem Rust.

1 Drawing Sheet

Botanical designation: *Berberis thunbergii.*
Cultivar denomination: 'KOREN'.

BACKGROUND OF THE INVENTION

The present invention relates to a new and distinct cultivar of *Barberry* plant, botanically known as *Berberis thunbergii* and hereinafter referred to by the name 'Koren'.

The new *Barberry* plant is a product of a planned breeding program conducted by the Inventor in Grand Haven, Mich. The objective of the breeding program was to develop new unique *Barberry* plants with attractive foliage, improved stress tolerance and resistance to Black Stem Rust (*Puccinia graminis*).

The new *Barberry* plant originated from an open-pollination in June, 2003 of *Barberry thunbergii* 'Golden Pygmy', not patented, as the female, or seed parent and an unknown selection of *Barberry thunbergii* as the male, or pollen, parent. The new *Barberry* plant was discovered and selected by the Inventor during the summer of 2006 as a single plant within the progeny of the stated open-pollination in a controlled environment in Grand Haven, Mich.

Asexual reproduction of the new *Barberry* plant by softwood cuttings in a controlled greenhouse environment in Grand Haven, Mich. since the summer of 2006 has shown that the unique features of this new *Barberry* plant are stable and reproduced true to type in successive generations of asexual reproduction.

SUMMARY OF THE INVENTION

Plants of the new *Barberry* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Koren'. These characteristics in combination distinguish 'Koren' as a new and distinct *Barberry* plant:

1. Compact and mounding plant habit.
2. Vigorous growth habit.
3. Freely branching habit.
4. Leaves that are yellow to yellow green in color.
5. Good garden performance and resistance to sun scald.
6. Resistance to Black Stem Rust.

Plants of the new *Barberry* can be compared to plants of the female parent, 'Golden Pygmy'. Plants of the new *Barberry* differ from plants of 'Golden Pygmy' in the following characteristics:

1. Plants of the new *Barberry* are more compact than plants of 'Golden Pygmy'.
2. Leaves of plants of the new *Barberry* are narrower than leaves of plants of 'Golden Pygmy'.
3. Plants of the new *Barberry* are more resistant to sun scald than plants of 'Golden Pygmy'.

Plants of the new *Barberry* can be compared to plants of the *Berberis thunbergii* 'Talago', disclosed in U.S. Plant Pat. No. 20,602. In side-by-side comparisons conducted in Grand Haven, Mich., plants of the new *Barberry* differed from plants of 'Talago' in the following characteristics:

1. Plants of the new *Barberry* were not as compact as plants of 'Talago'.
2. Plants of the new *Barberry* were more vigorous than plants of 'Talago'.
3. Leaves of plants of the new *Barberry* were narrower than and not as rounded as leaves of plants of 'Talago'.

Plants of the new *Barberry* can also be compared to plants of the *Berberis thunbergii* 'Aurea Nana', not patented. In side-by-side comparisons conducted in Grand Haven, Mich., plants of the new *Barberry* differed from plants of 'Aurea Nana' in the following characteristics:

1. Plants of the new *Barberry* were more compact than plants of 'Aurea Nana'.
2. Leaves of plants of the new *Barberry* were narrower than and not as rounded as leaves of plants of 'Aurea Nana'.
3. Plants of the new *Barberry* were more resistant to sun scald than plants of 'Aurea Nana'.

BRIEF DESCRIPTION OF THE PHOTOGRAPH

The accompanying colored photograph illustrates the overall appearance of the new *Barberry* plant showing the colors as true as it is reasonably possible to obtain in colored reproductions of this type. Colors in the photograph may differ slightly from the color values cited in the detailed botanical description which accurately describe the colors of the new *Barberry* plant. The photograph is a side perspective view of a typical plant of 'Koren' grown in a container.

DETAILED BOTANICAL DESCRIPTION

The aforementioned photograph and following observations, measurements and values describe plants grown during the spring and summer in an outdoor nursery in Grand Haven, Mich. and under cultural practices which closely approximate commercial production. Plants used for the photograph were 2.5 years old and plants used for the description were five years old. In the following detailed description, color references are made to The Royal Horticultural Society Colour Chart, 1995 Edition, except where general terms of ordinary dictionary significance are used.

Botanical classification: *Berberis thunbergii* 'Koren'.

Parentage:

*Female, or seed, parent.*—*Barberry thunbergii* 'Golden Pygmy', not patented.

*Male, or pollen, parent.*—Unknown selection of *Barberry thunbergii*, not patented.

Propagation:

*Type.*—By softwood cuttings.

*Time to initiate roots, summer.*—About 70 days at 20° C.

*Time to produce a rooted young plant, summer.*—About one year at 20° C.

*Root description.*—Fine to medium; somewhat fleshy and fibrous; yellow in color.

*Rooting habit.*—Freely branching; dense.

Plant description:

*Plant form and growth habit.*—Perennial shrub; compact and mounding plant habit; moderate growth rate and vigorous growth habit; freely branching habit with about 26 lateral branches developing per plant.

*Plant height.*—About 40 cm.

*Plant diameter* (*area of spread*).—About 56 cm.

Lateral branch description:

*Length.*—About 10 cm.

*Diameter.*—About 2 mm.

*Internode length.*—About 1 cm.

*Aspect.*—Erect to about 90° from vertical to arching.

*Strength.*—Strong, flexible.

*Texture.*—Smooth, glabrous.

*Color, developing.*—Close to 6C tinged with close to 46A; amount of reddish coloration will depend on environmental conditions.

*Color, fully developed.*—Close to 201D.

*Thorns.*—Quantity: About one thorn develops at each node. Length: About 8 mm. Width: About 1 mm. Color: Close to 8A; at the apex, close to 175A.

Foliage description:

*Arrangement.*—Alternate or whorled; simple.

*Length.*—About 2 cm.

*Width.*—About 1 cm.

*Shape.*—Oblanceolate to obovate.

*Apex.*—Mucronate.

*Base.*—Attenuate.

*Margin.*—Entire.

*Texture, upper and lower surfaces.*—Smooth, glabrous.

*Venation pattern.*—Pinnate.

*Color.*—Developing leaves, upper surface: Close to 150A. Developing leaves, lower surface: Close to 145B. Fully expanded leaves, upper surface: Depending on light level, close to 12A or 154A; venation, close to 145A; plants maintain yellow to yellow green coloration during the autumn. Fully expanded leaves, lower surface: Close to 13C; venation, close to 145A.

*Petiole.*—Length: About 1 cm. Diameter: About 2 mm. Texture, upper and lower surfaces: Smooth, glabrous. Color, upper and lower surfaces: Close to 12A or 154A.

Flower description: Flower initiation and development has not been observed on plants of the new *Barberry.*

Garden performance: Plants of the new *Barberry* have been observed to have excellent garden performance and to tolerate rain, wind and temperatures ranging from about −30° C. to about 32° C. In addition, plants of the new *Barberry* are resistant to sun scald.

Pathogen & pest resistance: Plants of the new *Barberry* have been observed to be resistant to Black Stem Rust (*Puccinia graminis*). Plants of the new *Barberry* have not been shown to be resistant to pests and other pathogens common to *Barberry* plants.

It is claimed:

1. A new and distinct *Barberry* plant named 'Koren' as illustrated and described.

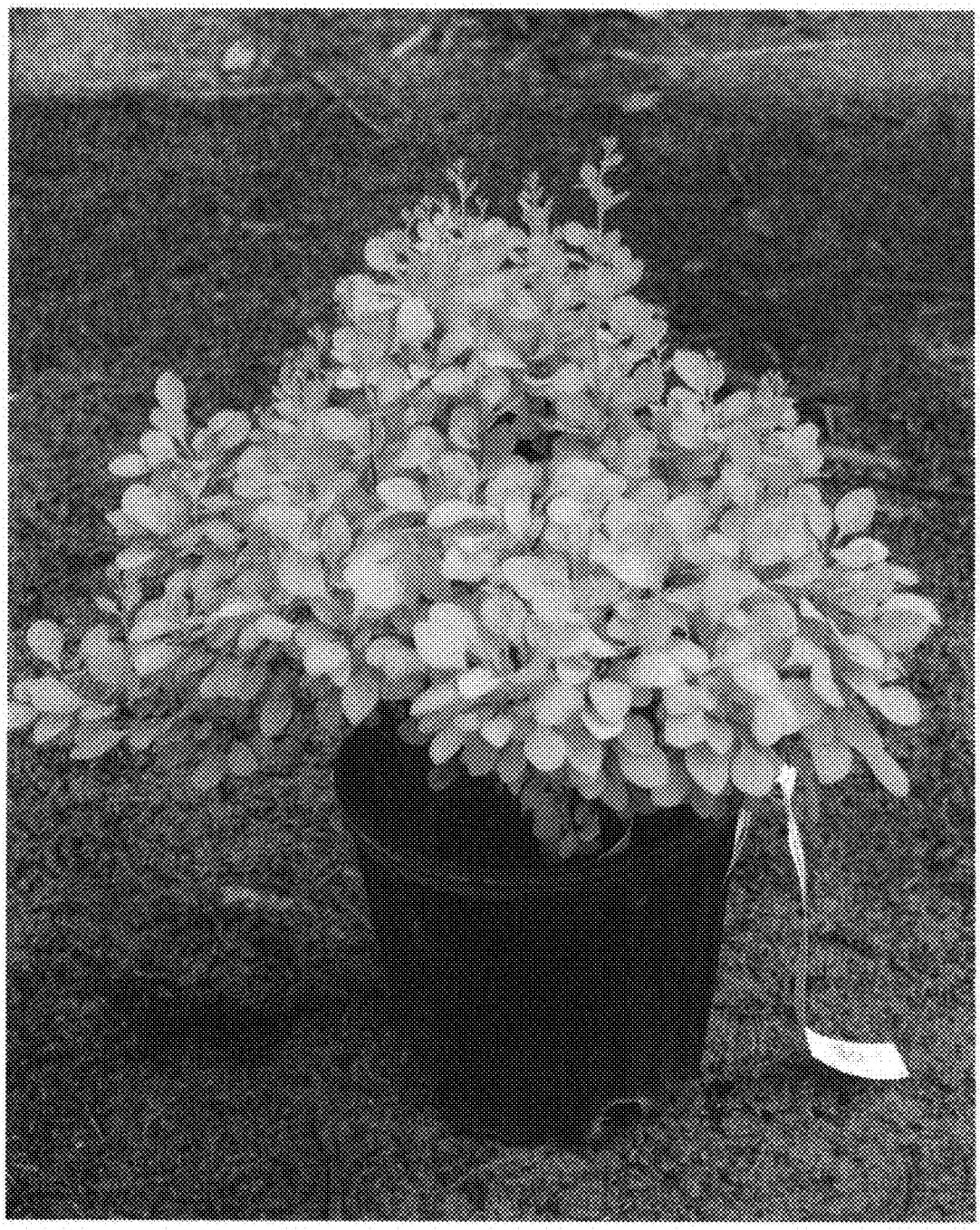

* * * * *